United States Patent [19]

Hager et al.

[11] Patent Number: 5,288,734
[45] Date of Patent: Feb. 22, 1994

[54] STABLE PARENTERAL SOLUTION OF 2-PHENYL-1,2-BENZISOSELENAZOL-3(2H)-ONE AND PROCESS FOR PRODUCING THE SAME

[75] Inventors: Joerg Hager; Andrea M. Huether; Joachim Roeding, all of Cologne, Fed. Rep. of Germany

[73] Assignee: A. Nattermann & CIE GmbH, Fed. Rep. of Germany

[21] Appl. No.: 740,861

[22] Filed: Jul. 31, 1991

Related U.S. Application Data

[63] Continuation of Ser. No. 428,870, Oct. 30, 1989, abandoned.

[30] Foreign Application Priority Data

Oct. 29, 1988 [DE] Fed. Rep. of Germany ....... 3836892

[51] Int. Cl.$^5$ .............................................. A61K 31/41
[52] U.S. Cl. .................................................... 514/359
[58] Field of Search .......................................... 514/359

[56] References Cited

U.S. PATENT DOCUMENTS

| | | | |
|---|---|---|---|
| 4,352,799 | 10/1982 | Renson et al. | 424/244 |
| 4,711,961 | 12/1987 | Welter | 548/121 |
| 4,784,994 | 11/1988 | Romer et al. | 514/183 |
| 4,778,8156 | 10/1988 | Cash | 514/359 |

FOREIGN PATENT DOCUMENTS 0249735  12/1987  European Pat. Off. ............ 548/121

OTHER PUBLICATIONS

Handbook of Pharmaceutical Excipients, p 165, A.P.A. Wash. D.C. 1986.
Bulletin de la Soc. Chim. de France, 1976 (7/8), S. 1124–1126.

Primary Examiner—Robert Gerstl
Attorney, Agent, or Firm—Pearne, Gordon, McCoy & Granger

[57] ABSTRACT

The present invention is related to new parenteral preparations of 2-phenyl-1,2-benzisoselenazol-3(2H)-one (Ebselen) comprising additionally one or several phospholipids and, possibly, one or several auxiliary agents. The invention is further related to a process for producing such solutions and their use in the preparation of drug preparations ob Ebselen.

4 Claims, No Drawings

STABLE PARENTERAL SOLUTION OF 2-PHENYL-1.2-BENZISOSELENAZOL-3(2H)-ONE AND PROCESS FOR PRODUCING THE SAME

This is a continuation of application Ser. No. 07/428,879, filed Oct. 30, 1989 now abandoned.

The present invention is related to new solutions which may be parenterally administered and which comprise 2-phenyl 1.2-benzisoselenazol-3(2H)-one (Ebselen) in combination with one or several phospholipids in a weight proportion of from 1:2500 to 1:15 and, possibly, one or several auxiliary agents. The invention is further related to the production of such solutions as well as their use in the production of drug preparations comprising 2-phenyl-1.2-benzisoselenazol-3(2H)-one (Ebselen) and one or several phospholipids.

Ebselen is a known product (DE-PS 3027073, U.S. Pat. No. 4,352,799). It may be produced by the process of R. Weber and M. Renson, Bulletin de la Soc. Chim. de France 1976 (7/8), pgs. 1124–1126, by subjecting 2-methylseleno-N-phenyl-benzamide to reaction with phosphorous pentachloride and subsequently hydrolysing the obtained product. Preparations comprising Ebselen may be used in the treatment of numerous diseases such as the prophylaxis and therapy of infectious diseases, the therapy of malignant tumors (DE-OS 3638124), for stimulating the immune system or for the treatment of selenium deficiency diseases. Further attention is drawn to the application of the anti-arteriosclerotic and anti-inflammatory properties of Ebselen and their application in the therapy of rheumatic diseases (DE-OS 3027073, U.S. Pat. No. 4,352,799). Ebselen is furthermore an important agent useful in the therapy of deficiencies caused by oxidative stress (DE-OS 3616923), European publication 0249735 such is liver deficiencies, cardiac infarction, psoriasis and radiation sickness. There is known also a drug preparation for the topical use of Ebselen (DE-OS 3620674, U.S. Pat. No. 4,784,994), which may be used in the external treatment of inflammatory and allergic skin diseases such as psoriasis.

The broad spectrum of properties is in contrast to a very low solubility of Ebselen in water. Due thereto the use of Ebselen in the form of parenteral solutions is prevented. Preparations comprising organic solvents containing Ebselen dissolved therein do not provide satisfactory results because diluting such solutions with water for injections or with physiological saline solution cause precipitation of crystals of Ebselen.

It has now been found that surprisingly stable aqueous solutions of 2-phenyl-1.2-benzisoselenazol-3(2H)-one (Ebselen) having a physiological pH may be produced by combining Ebselen with one or several natural or synthetic phospholipids and this in a weight proportion of Ebselen to phospholipid amounting to a ratio ranging from 1:2500 to 1:15. Further auxiliary agents may be added.

In this way, new aqueous solutions of Ebselen in combination with one or several phospholipids are formed. Such solutions are very suitable for parenteral administration (for instance for intramuscular or intravenous administration) and such solutions show a long duration of action.

For producing such solutions, the components thereof are added to each other and stirred to produce homogenous solutions in usual manners, for instance by aid of high pressure homogenizers. In some instances it is possible to obtain the solutions by simple stirring. Another possibility to produce the solutions is treatment with ultrasonic methods or by using the so called "French Press".

Supplements to produce isotonicity may be added before or after the preparation of the homogenous solutions. Such products are sodium chloride, glucose or the like. It may be advantageous to add a base, for instance soda lye or a buffer agent in order to produce a pH close to the physiological pH. The solutions thus prepared may be sterilized in usual manners and filled into ampoules as usual.

In view of the sensitivity of the phospholipids to light and oxygen, it may be preferable to work with the exclusion of oxygen and in an inert atmosphere, and with the exclusion of light.

Both natural and synthetic phospholipids may be used. Natural phospholipids (of plant or animal origin) are in particular phosphatidyl choline, phosphatidyl ethanolamine, phosphatidyl inositol, phosphatidyl glycol, cardiolipine or plasmalogens, which products may be recovered from soybeans or from eggs. Further useful are mixtures of several such phospholipids such as the trade products Phospholipon ® 100: (95% natural phosphatidyl choline from soybeans)

Phospholipon ® 100 H: (98% fully hydrogenated phosphatidyl choline from soybeans)

Phospholipon ® 80: (phospholipids from soybeans comprising 76% of phosphatidyl choline and 12% of phosphatidyl ethanolamine).

Synthetic phosphatides are for instance:
dihexadecanoylphosphatidylcholine,
ditetradecanoylphosphatidylcholine,
dioleylphosphatidylcholine,
dilinolylphosphatidylcholine,
in particular
dipalmitoylphosphatidylcholine and
dipalmitoylphosphatidylglycerol.

Auxiliary agents are for instance cholesterol, derivatives of bile acids and salts thereof, benzylalcohol, neutral oils (Miglyol 812) and glycerol.

The production of the preparations according to the present invention is further illustrated in the following examples.

EXAMPLE 1

| | |
|---|---|
| Ebselen | 0.110 g |
| DPPC (dipalmitoylphosphatidylcholine) | 13.330 g |
| DPPG (dipalmitoylphosphatidylglycerol) | 1.330 g |
| cholesterol | 6.450 g |
| buffering agent to pH4 | up to 1000 ml |

Ebselen, DPPC, DPPG and cholesterol are dissolved in a mixture of 1 part of methanol and 1 part of chloroform. The solvent is removed and the resulting film is hydrated with buffer under an inert gas. Glas beads are added and liposomes are formed with stirring. They are filtered in usual manner under sterile conditions and filled into ampoules.

EXAMPLE 2

| | |
|---|---|
| Ebselen | 0.150 g |
| DPPC | 18.180 g |
| DPPG | 1.818 g |
| cholesterol | 8.790 g |

-continued

| | |
|---|---|
| water for injections | up to 1000 ml |

The products are mixed and further processed as described in example 1.

EXAMPLE 3

| | |
|---|---|
| Ebselen | 0.250 g |
| DPPC | 30.300 g |
| DPPG | 3.030 g |
| cholesterol | 14.650 g |
| buffering agent | up to 1000 ml |

The products are mixed and further processed as described in example 1.

EXAMPLE 4

| | |
|---|---|
| Ebselen | 0.330 g |
| DPPC | 39.970 g |
| DPPG | 3.997 g |
| cholesterol | 19.338 g |
| buffering agent | up to 1000 ml |

The products are mixed and further processed as described in example 1.

EXAMPLE 5

| | |
|---|---|
| Ebselen | 0.400 g |
| DPPC | 48.480 g |
| DPPG | 4.848 g |
| cholesterol | 23.440 g |
| buffering agent | up to 1000 ml |

The products are mixed and further processed as described in in example 1.

EXAMPLE 6

| | |
|---|---|
| Ebselen | 0.430 g |
| DPPC | 50.170 g |
| DPPG | 5.017 g |
| cholesterol | 24.112 g |
| buffering agent | up to 1000 ml |

The products are mixed and further processed as described in in example 1.

EXAMPLE 7

| | |
|---|---|
| Ebselen | 0.100 g |
| Phospholipon ® 100 | 45.215 g |
| sodiumdesoxycholate | 17.621 g |
| bezylalcoh | 15.700 g |
| water for injections | up to 1000 ml |

Ebselen and Phospholipon 100 are dissolved in ethanol. After removal of the solvent under vacuum, the resulting mixture is stirred into a solution of sodium deoxycholate. After the addition of benzyl alchohol and water as described in example 1, the solution is filtered under sterile conditions and filled into ampoules.

EXAMPLE 8

| | |
|---|---|
| Ebselen | 0.300 g |
| Phospholipon ® 100 | 116.900 g |
| sodiumdesoxycholate | 45.900 g |
| benzylalcohol | 15.700 g |
| water for injections | up to 1000 ml |

The products are mixed and further processed as described in in example 7.

EXAMPLE 9

| | |
|---|---|
| Ebselen | 0.300 g |
| Phospholipon ® 100 | 116.900 g |
| glycocholic acid | 58.200 g |
| NaOH | 5.000 g |
| benzylalcohol | 15.700 g |
| water for injections | up to 1000 ml |

EXAMPLE 10

| | |
|---|---|
| Ebselen | 0.300 g |
| Phospholipon ® 80 | 116.900 g |
| imrocholic acid | 64.370 g |
| NaOH | 5.000 g |
| benzylalcohol | 15.700 g |
| water for injections | up to 1000 ml |

The products are mixed and further processed as described in in example 7.

EXAMPLE 11

| | |
|---|---|
| Ebselen | 0.450 g |
| Phospholipon ® 100 | 110.440 g |
| sodium cholate | 40.125 g |
| benzylalcholo | 15.700 g |
| water for injections | up to 1000 ml |

The products are mixed and further processed as described in in example 7.

EXAMPLE 12

| | |
|---|---|
| Ebselen | 0.500 g |
| Phospholipon ® 80 | 108.700 g |
| water for injections | up to 1000 ml |

Ebselen and Phospholipon ® 100 are dispersed with stirring in water for injection purposes. The resulting mixture is treated in the high pressure homogenizer. The further subsequent filtration under sterile conditions and filling into ampoules is executed as described in example 1.

EXAMPLE 13

| | |
|---|---|
| Ebselen | 0.420 g |
| Phospholipon ® 80 | 111.250 g |
| water for injections | up to 1000 ml |

The products are mixed and further processed as described in in example 12.

EXAMPLE 14

| Ebselen | 0.200 g |
|---|---|
| lecithin | 20.000 g |
| Miglyol 812 | 170.000 g |
| glycerol | 16.000 g |
| water for injections | up to 1000 ml |

Ebselen is dissolved in Miglyol 812 and lecithin (solution I). Glycerol is added to the water for injection purposes (solution II). Both solutions are mixed and treated in the high pressure homogenizer. The resulting emulsion is stirilized in the autoclave and filled into ampoules as usual.

EXAMPLE 15

| Ebselen | 0.500 g |
|---|---|
| lecithin | 24.000 g |
| Miglyol 812 | 200.000 g |
| glycerol | 32.000 g |
| water for injections | up to 1000 ml |

The products are mixed and further processed as described in in example 14.

EXAMPLE 16

| Ebselen | 1.000 g |
|---|---|
| lecithin | 24.000 g |
| Miglyol 812 | 200.000 g |
| glycerol | 32.000 g |
| water for injections | up to 1000 ml |

The products are mixed and further processed as described in in example 14.

EXAMPLE 17

| Ebselen | 2.000 g |
|---|---|
| lecithine | 32.000 g |
| Miglyol 812 | 220.000 g |
| glycerol | 37.000 g |
| water for injections | up to 1000 ml |

The products are mixed and further processed as described in in example 14.

We claim:

1. Stable injectable solution of 2-phenyl-1.2-benzisoselenazol-3(2H)-one, characterized in that they contain a water-soluble combination of 2-phenyl-1.2-benzisoselenazol-3(2H)-one with one or several phospholipids, the weight proportion of 2-phenyl-1.2-benzisoselenazol-3(2H)-one and the phospholipid or phospholipids in the solution being between 1:2500 to 1:15.

2. Solution according to claim 1, characterized in that the phospholipid or the phospholipids represent natural or synthetic phospholipids.

3. Solution according to claim 2, characterized in that it comprises as natural phospholipid the compound soybean lecithin or egg lecithin or a highly purified fraction thereof.

4. Solution according to claim 2, characterized in that the synthetic phospholipid is phosphatidyl choline, phosphatidyl glycerol or a mixture thereof.

* * * * *